United States Patent [19]
Cellini et al.

[11] Patent Number: 5,959,181
[45] Date of Patent: Sep. 28, 1999

[54] METHOD OF PREPARATION OF TRANSGENIC PLANTS RESISTANT TO VIRAL INFECTIONS AND SO OBTAINED PLANTS

[75] Inventors: Francesco Cellini, Matera; Pasquale Domenico Grieco, Pisticci, both of Italy

[73] Assignee: Metapontum Agrobios S.c.r.l., Matera, Italy

[21] Appl. No.: 08/854,170

[22] Filed: May 9, 1997

[51] Int. Cl.$^6$ ............ C12N 15/05; C12N 15/33; C12N 15/64; A01H 1/00

[52] U.S. Cl. ............ 800/301; 800/278; 800/279; 800/280; 800/286; 800/295; 800/298; 536/24.1; 536/24.5; 536/23.72; 435/320.1; 435/410; 435/419; 435/468

[58] Field of Search .................... 800/205, 278, 800/279, 280, 286, 295, 298, 301; 435/172.3, 320.1, 410, 419, 468; 536/24.1, 24.5, 23.72

[56] References Cited

U.S. PATENT DOCUMENTS 5,466,788   11/1995   Ahlquist et al. .................... 536/24.1

FOREIGN PATENT DOCUMENTS

| | | |
|---|---|---|
| 0 279 433 | 8/1988 | European Pat. Off. . |
| 0 421 376 | 4/1991 | European Pat. Off. . |
| 0 425 004 | 5/1991 | European Pat. Off. . |
| 0 479 180 | 4/1992 | European Pat. Off. . |
| WO 89/05858 | 6/1989 | WIPO . |
| WO 91/13994 | 9/1991 | WIPO . |
| WO 94/19476 | 9/1994 | WIPO . |
| WO 94/29464 | 12/1994 | WIPO . |

OTHER PUBLICATIONS

Chemical Abstracts, vol. 113, No. 15, AN 127723, 1990, CN 1,033,645, Jul. 5, 1989.

Clayton C. Huntley, et al., vol. 192, pp. 290–297, "Minus Sense Transcripts of Brome Mosaic Virus RNA–3 Intercistronic Region Interfere with Viral Replication", 1993.

P. A. Powell, et al., Proceedings of the National Academy of Sciences of the USA, vol. 86, No. 18, pp. 6949–6952, "Protection Against Tobacco Mosaic Virus in Transgenic Plants that Express Tobacco Mosaic Virus Antisense RNA", Sep. 1989.

Maria Cuozzo, et al., Biotechnology, vol. 6, pp. 549–557, "Viral Protection in Transgenic Tobacco Plants Expressing the Cucumber Mosaic Virus Coat Protein or its Antisense RNA", May 1988.

M. Ali Rezaian, et al., Plant Molecular Biology, vol. 11, pp. 463–471, "Anti–Sense RNA's of Cucumber Mosaic Virus in Transgenic Plants Assessed for Control of the Virus", Apr. 19, 1988.

Arlen Nelson, et al., Gene, vol. 127, pp. 227–232, "Tobacco Mosaic Virus Infection of Transgenic Nicotiana Tabacum Plants is Inhibited by Antisense Constructs Directed at the 5' Region of Viral RNA", 1993.

Bruno Zaccomer, et al., Gene, vol. 136, pp. 87–94, "Transgenic Plants that Express Genes Including the 3' Untranslated Region of the Turnip Yellow Mosaic Virus (TYMV) Genome are Partially Protected Against TYMV Infection", 1993.

Z.R. Sung, et al., *Science*, "EMF, An Arabidopsis Gene Required for Vegetative Shoot Development", vol. 258, pp. 1645–1647, XP 002047279.

Joseph G. Atabekov, et al., vol. 309, pp. 23–24, "New Strategies for Construction of Virus Resistant Transgenic Plants", Apr. 1995.

Cuozzo et al. Viral protection in transgenic tobacco plants expressing the cucumber mosaic virus coat protein or its antisense RNa. BioTechnology. 6(5):549–557, May 1988.

Graves et al. Characterization of defective RNAs derived from RNA 3 of the Fny strain of cucumber mosaic cucumovirus. Journal of Virology. 69(8):4746–4751, Aug. 1995.

Hayakawa et al. Nucleotide sequence analysis of cDNA encoding the coat protein of cucumber mosaic virus: genome organization and molecular features of the protein. Gene. 71:107–114, 1988.

Quemada et al. Nucleotide sequences of the coat protein genes and flanking regions of cucumber mosaic virus strains C and WL RNA 3. Journal of General Virology. 70:1065–1073, 1989.

Anderson et al. RNA 4 sequences from cucumber mosaic virus subgroups I and II. Gene. 161:293–294, 1995.

Smith et al. Antisense RNA inhibition of polygalacturonase gene expression in transgenic tomatoes. Nature. 334:724–726, Aug. 1988.

*Primary Examiner*—Elizabeth F. McElwain
*Assistant Examiner*—Ashwin D. Mehta
*Attorney, Agent, or Firm*—Oblon, Spivak, McClelland, Maier & Neustadt, P.C.

[57] ABSTRACT

The present invention relates to a method of preparation of transgenic plants resistant to viral infections by introducing into the genoma of a host plant an antisense gene construct constituted by: the domain F of the subgenomic promoter of a viral RNA; a leader sequence of a viral ORF, downstream from said subgenomic promoter; the gene encoding a viral coat protein, downstream from said leader sequence; and the 3'-terminal region of a viral RNA, downstream from said gene. The present invention also relates to a recombinant vector comprising a promoter functional in a host plant, and, operably linked to this promoter, the antisense gene construct of the present invention.

7 Claims, 6 Drawing Sheets

Fig.1

| | | | | |
|---|---|---|---|---|
| TGGTCTCCTT | TTGGAGGCCC | CACAAAAGTG | GGGGGGCACC | 40 |
| CGTACCCTGA | AACTAGCACG | TTGTGCTAGA | AGTACACGGA | 80 |
| CCGAAGTCCT | TCCGAAGAAA | CCTAGGAGAT | GGTTTCAAAG | 120 |
| GTGCCTCAGA | GACTTGTAAG | TCTACTGGCG | TAGATTTCTC | 160 |
| TACGACTGAC | CATTTTAGCC | GTAAGCTGGA | TGGACAACCC | 200 |
| GTTCACCACA | GTGTGTTTAG | TGACTTCAGA | CAGTTTATAG | 240 |
| CAGAACTGCC | AACTCAGCTC | CCACCACAGA | GTCGAAGGGA | 280 |
| GGATTCTGGA | AACGCGGAAT | CAGACTGGGA | GCACCCAAGA | 320 |
| TGTGGGAATG | CGTTGGTGCT | CGATGTCAAC | ATGAAGTACT | 360 |
| AGCTCGTCGG | TCTCAAGCGT | ATCGTCTTTT | GAATACACGA | 400 |
| GGACGGCGTA | CTTTCTCATG | TCACCTATAT | CAGCGCGCAT | 440 |
| CGCCGAAAGA | TCATACAACA | ATTTGTTGTT | GGCTTGGACT | 480 |
| CCAGATGCGG | CATACTGATA | AACCAGTACC | GGTGAGGCTC | 520 |
| CGTCCGCGAA | CATAGCAGAG | ATGGCGGCAA | CGGATAAGTC | 560 |
| CGAGGAGGCA | GGAACTTTAC | GGACTGTCAC | CCACACGGTA | 600 |
| GAATCAAATT | TCGGCAAAGG | ATTAACTCGA | ATTTGAATGC | 640 |
| GCGAAACAAG | CTTCTTATCA | TATTCCGTGA | CTGAATCAGG | 680 |
| TAGTAACAAC | CTTTTACCGT | AATAAGACTC | ACGGTCTATT | 720 |
| TTTGGTGGCT | TTAGGGTTAT | AGATGTGAAC | GTGTACCCAG | 760 |
| GTCTACAGCG | TTCACTCCCT | ACAAAGGTTG | GGTGGTTAAT | 800 |
| AGTTGGACGA | CCAGCTGCTA | ACGTCTTATT | AAGTCGCGAA | 840 |
| AGCTGCTGCG | ACAAGACTCT | AAAGTTAGCA | TCCGCGGAGG | 880 |
| AGGGGGCGGA | GCGGGAACCA | CGACGCGGAC | GACGTCGACG | 920 |
| GTTACGACCA | GCACTGGTTG | ATTCAGATTT | GTCCATGACT | 960 |
| CGACTCAATT | CTACGACACA | AAAGAGAAAA | CACAGCACAC | 1000 |
| ACACTCTCTA | TATAGTCAGT | AGACAATAAC | GCAATCTCGC | 1040 |
| GGAGAAGCAT | CCATGAGAAA | GTAAGG | | 1066 |

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1067 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TGGTCTCCTT TTGGAGGCCC CACAAAAGTG GGGGGGCACC CGTACCCTGA AACTAGCACG          60

TTGTGCTAGA AGTACACGGA CCGAAGTCCT TCCGAAGAAA CCTAGGAGAT GGTTTCAAAG         120

GTGCCTCAGA GACTTGTAAG TCTACTGGCG TAGATTTCTC TACGACTGAC CATTTTAGCC         180

GTAAGCTGGA TGGACAACCC GTTCACCACA GTGTGTTTAG TGACTTCAGA CAGTTTATAG         240

CAGAACTGCC AACTCAGCTC CCACCACAGA GTCGAAGGGA GGATTCTGGA AACGCGGAAT         300

CAGACTGGGA GCACCCAAGA TGTGGGAATG CGTTGGTGCT CGATGTCAAC ATGAAGTACT         360

AGCTGGTCGG TCTCAAGCGT ATCGTCTTTT GAATACACGA GGACGGCGTA CTTTCTCATG         420

TCACCTATAT CAGCGCGCAT CCAGATGCGG TCATACAACA ATTTGTTGTT GGCTTGGACT         480

CCAGATGCGG CATACTGATA AACCAGTACC GGTGAGGCTC CGTCCGGAAC ATAGCAGAGA         540

TGGCGGCAAC GGATAAGTCC GAGGAGGCAG GAACTTTACG GACTGTCACC CACACGGTAG         600

AATCAAATTT CGGCAAAGGA TTAACTCGAA TTTGAATGCG CGAAACAAGC TTCTTATCAT         660

ATTCCGTGAC TGAATCAGGT AGTAACAACC TTTTACCGTA ATAAGACTCA CGGTCTATTT         720

TTGGTGGCTT TAGGGTTATA GATGTGAACG TGTACCCAGG TCTACAGCGT TCACTCCCTA         780

CAAAGGTTGG GTGGTTAATA GTTGGACGAC CAGCTGCTAA CGTCTTATTA AGTCGCGAAA         840

GCTGCTGCGA CAAGACTCTA AAGTTAGCAT CCGCGGAGGA GGGGCGGAG CGGGAACCAG          900

CGACGCGGAC GACGTCGACG GTTACGACCA GCACTGGTTG ATTCAGATTT GTCCATGACT         960

CGACTCAATT CTACGACACA AAAGAGAAAA CACAGCACAC ACACTCTCTA TATAGTCAGT        1020

AGACAATAAC GCAATCTCGC GGAGAAGCCA TCCATGAGAA AGTAAGG                     1067
```

(2) INFORMATION FOR SEQ ID NO:2:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "SYNTHETIC DNA"

(xi) SEQUENCE DESCRIPTION: SEQ ID NO:2:

CCGGATCCCC TTACTTTCTC ATGG                              24

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETHIC DNA"

(xi) SEQUENCE DESCRIPTION: SEQ ID NO:3:

CCGGATCCTG GTCTCCTTTT GGAGGCCCCA                        30

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:4:

TGGTCTCCTT TTGGAGGCCC                                   20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:5:

GTAATCTTAC CACTTGTGTG                                   20

METHOD OF PREPARATION OF TRANSGENIC PLANTS RESISTANT TO VIRAL INFECTIONS AND SO OBTAINED PLANTS

BACKGROUND OF THE INVENTION

1. Field of the Invention

The present invention relates to a method of preparation of transgenic plants resistant to viral infections, a recombinant vector and so obtained transgenic plants.

2. Description of the Related Art

Many plant diseases are caused by RNA viruses, such as, e.g., tobacco mosaic virus (TMV), cucumber mosaic virus (CMV), potato virus (PV), and so forth. Most viral infections reduce crop yields and, sometimes, may even cause catastrophic effects causing considerable financial losses.

CMV, a virus belonging to Cucumovirus type, is diffused in nature by flying carriers, i.e., aphids. From these, at least 60 different species are capable of collecting the virus from an infected plant, and retransmitting it directly to a healthy plant, without a lag period inside the insect (non-persistent transmission).

CMV is a polyphagous virus, certainly from phytoviruses, the one with the widest ascertained range of hosts, approximately a thousand of different species (Palukaitis et al., Adv. In Virus Res. 41:281–348, 1992). It derives that the inoculum is always present in nature, both in wild and cultivated plants, acting as reservoirs from which aphids collect their virus supply.

The disease caused by CMV manifests with different symptoms: reduced development of the plant, foliar chlorosis and several malformations both in aerial parts of the plant and in fruits. However, the most serious pathology, caused by some necrogenic viral strains, appears in tomato and is given the name of "lethal necrosis".

From a molecular viewpoint, CMV displays a tripartite RNA genome, arranged inside the coat protein (CP). Genomic RNA's, which are single-stranded and have mRNA(+) polarity, are classified, with reference to their molecular weight, into RNA-1 (3.4 Kb), RNA-2 (3.0 Kb) and RNA-3 (2.4 Kb). Furthermore, in viral preparations, a fourth RNA is present which encodes the coat protein, is referred to as "sub-genomic RNA-4" of 1,027 Kb from RNA-3 and is co-linear with this.

RNA 1 and 2 are monocistronic and encode two proteins, respectively of 991 and 839 aminoacids, correlated with virus replication activity. RNA-3 is dicistronic and, at its 5' terminal region encodes a protein implied in virus transportation into the plant, and at its 3'-terminal region contains the genes encoding the coat protein (CP). In intercistronic region of RNA-3 the sub-genomic promoter is present which is important in vivo for the formation of sub-genomic RNA-4 (+) on which the coat protein is translated. In fact, replicase recognizes the promoter sequence on (-) strand of RNA-3, thus securing the synthesis of RNA-4.

In some viral extracts, a small extragenomic RNA is furthermore present, which is known as "RNA-5" or, more commonly, CARNA-5, belonging to the class of satellite RNAs. CARNA-5 performs an important biologic function because it is capable of modulating the symptoms of CMV infection, and namely, rendering them either lighter or more serious. In fact, two types of CARNA-5 exist, which are referred to as "necrogenic" the one, and "non necrogenic" the other (also said "benign"), owing to its capability of inducing, or less, necrotic symptoms in infected plants.

Some valuable agricultural practices, as rotation of crops and removal of weeds and crop's residues or use of insecticides, may be able to control the viral attack, but only partially. In fact, a fast assay bite on a plant treated with insecticides is enough to infect it, also if the aphid subsequently dies.

Therefore, alternative solutions were proposed in the art for combatting phytoviruses, in general, and CMV in particular, which are essentially based on the introduction of non-conventional resistances, or transgenic resistance, and comprise:

1) Using benign variants of CARNA-5 for a plant preimmunization or vaccination.

This method consists in infecting the plants simultaneously with the pathogenic virus and benign satellite RNA in order to create a tolerance to this virus. The variability of the compounded viral genomes and the high recombination frequency, which may be limited only by means of a control of the vaccination system which is very laborious and burdensome, display however potential risks. In fact, the virus used for the vaccination may possibly diffuse into the surrounding environment, in which it could cause synergisms with other pathogens, thus causing damages to more sensitive species. Therefore, this method cannot be applied on large areas.

2) Introduction of satellite RNA into the genome of the plant

In order to avoid the problems derived from preinoculation, the plants have been modified by adding satellite RNA to their genome. In the resulting plants, a reduction of symptoms caused by virus could be observed.

However, the genetic transformation with satellite RNA does not exclude the risk of a back mutation. A necrogenic variant of CARNA-5 possibly arising could be rapidly diffused throughout the surrounding environment through the natural infection ways, with serious consequences. Furthermore, owing to the satellite-virus-plant interaction, apparently "benign" satellites could cause damages to different plants from source plants.

3) Use of the gene encoding the coat protein.

Recently, it was demonstrated for different viral species with tripartite or monopartite RNA, that, through the introduction into plants of RNA-4 gene encoding the coat protein, transgenic plants can be obtained which display a strong decrease in disease symptoms when they are exposed to infections with the same virus.

However, also this method is not free from drawbacks. In fact, the coat protein produced inside the vegetable tissues can encapsidate foreign RNA to virus (heterologous encapsidation), thus originating new viral particles with can be acquired and diffused within the surrounding environment by the carriers (Palukaitis et al., Adv. In Virus Res. 41:281–348; 1992).

4) Use of antisense RNA

Another strategy used in order to obtain transgenic plants resistant to determined viruses consists in inserting into the plant a DNA sequence which is complementary to a portion of the viral genome in antisense orientation (not encoding). Unfortunately, the use of such a strategy gave unsatisfactory results. In fact, transgenic tobacco plants, obtained by using the antisense gene of the coat protein of CMV and PVX, displayed a tolerance to virus only when they were infected with low inoculum concentrations (Cuozzo et al., Biotechnol., 6:549–557, (1988); Hemenway et al., EMBO J. 7:1273–1280, 1988). Furthermore, discouraging results were obtained when antisense genes were used which were capable of complementing with different domains of genomic RNAs of CMV. In fact, only in one case low resistance levels were observed (Rezaian et al., Plant Molecular Biology, 11:463–471, 1988).

SUMMARY OF THE INVENTION

It has now been found that the drawbacks displayed by the prior art, as discussed hereinabove, can be overcome by means of the method according to the present invention, which is based on the use of an antisense gene construct which allows transgenic plants to be obtained which display a complete resistance to virus, in absence of production of coat protein.

More particularly, it was found that the interfering activity performed by the antisense of F domain of the sub-genomic promoter of a viral RNA associated with the antisense activity performed by the gene encoding a coat protein allows transgenic plants to be obtained which are resistant to viral infections. This resistance manifests itself with a complete absence of symptoms and with an evident incapability of virus spreading from the inoculation site to the other plant parts.

In accordance therewith, the present invention relates to a method of preparing transgenic plants resistant to viral infections by means of the introduction into the genome of plants sensible to said infections, of an antisense gene construct constituted by: the F domain of the sub-genomic promoter of a viral RNA; a leader sequence of a viral ORF, downstream from said sub-genomic promoter; the gene encoding a viral coat protein, downstream from said leader sequence; and the 3'-terminal region of a viral RNA, downstream from said gene.

The invention furthermore relates to a recombinant vector comprising a promoter functional in a host plant and, operably linked to said promoter, the antisense gene construct according to the present invention.

A further object of the present invention are transgenic plants resistant to viral infections, obtained by the method according to the present invention.

BRIEF DESCRIPTION OF FIGURES

FIG. 1: the sequence is reported of the 1066 bp long fragment of cDNA clone of RNA-3 of CMV, wherein:

the region spanning from nucleotide 1 to 299 corresponds to the untranslated 3'-terminal region (UTR); the region spanning from nucleotide 300 to nucleotide 955 corresponds to the gene encoding the coat protein, the region spanning from nucleotide 956 to 1029 corresponds to the leader sequence of the coat protein, and the region spanning from nucleotide 1030 to 1066 corresponds to the F sequence of the sub-genomic promoter (SGP).

Figure 2A:
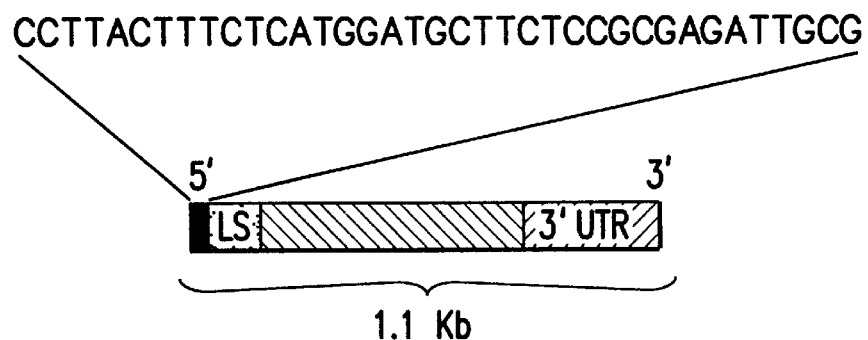
Figure 2B:
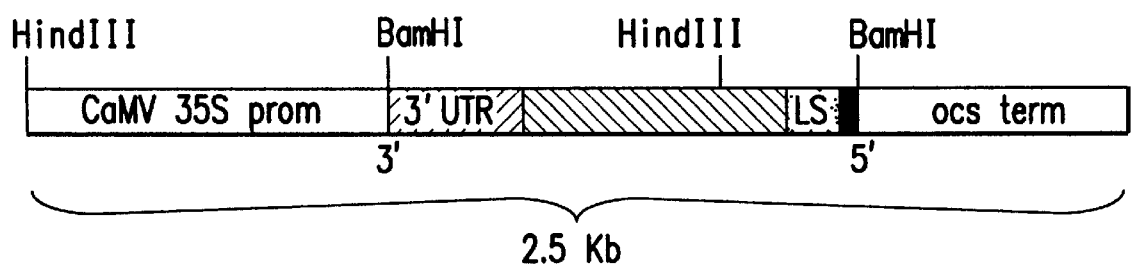

FIG. 2: in (A), top, the defective gene SGP-CP is schematically represented in sense (+) orientation, wherein: F indicates the homonimous region F of the sub-genomic promoter; LS is the leader sequence of the coat protein; CP is the sequence encoding the coat protein and UTR is the untranslated, tRNA-like 3'-terminal region.

In (B) the expression cassette of pJAZZ-CP-SGP(-) vector is reported.

Figure 3:
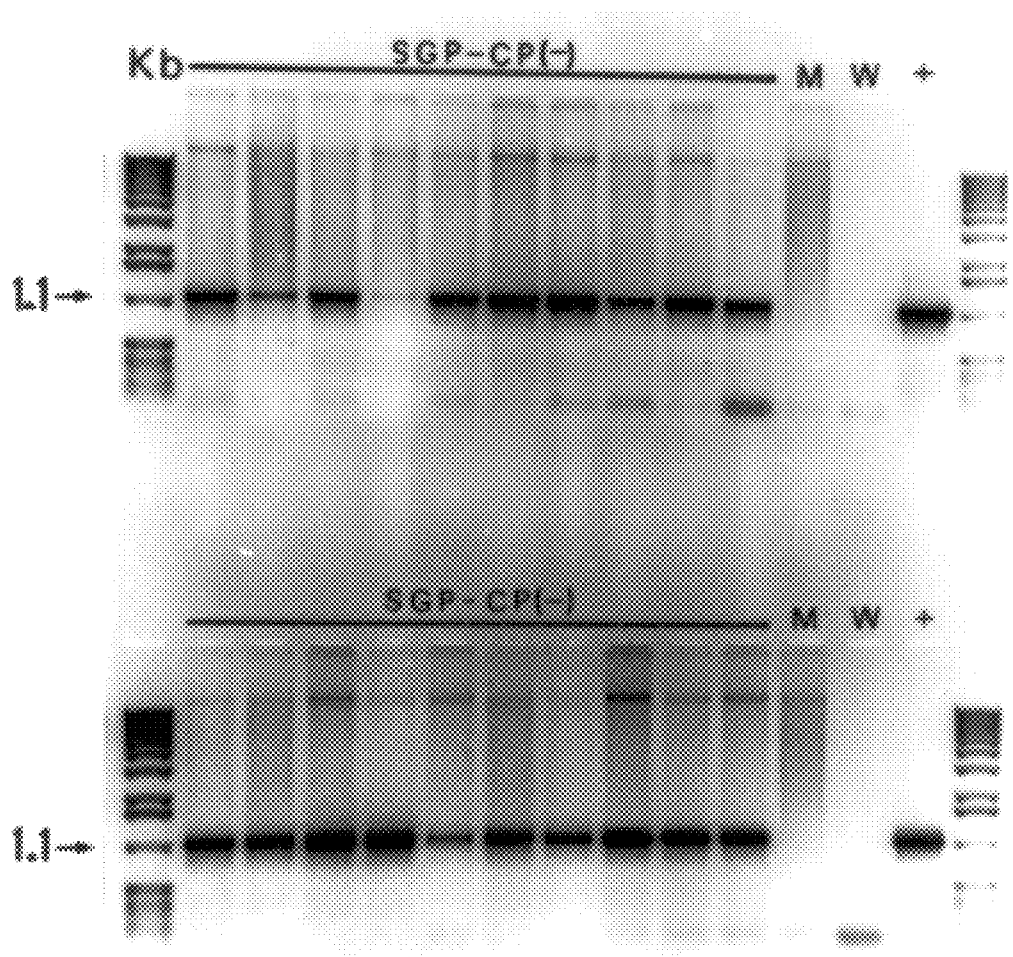

FIG. 3: the photograph is reported of an agarose gel on which the products from PCR (polymerase chain reaction) carried out on genomic DNA extracted from T0 clones of *Nicotiana tabacum* cv. W38 transformed with pJAZZ-SGP-CP(-) vector were loaded and submitted to electrophoresis. All clones assayed displayed the 1,1 Kb band. The letter M indicates the well into which the product was introduced which was derived from the reaction on genomic DNA extracted from a non-transformed W38 tobacco plant; the letter W indicates te well to which the reaction mixture without genomic DNA was charged; the symbol "+" indicates the positive control well to which the reaction product was added which was obtained by PCR using pJAZZ-SGP-CP(-) as the templant.

Figure 4:
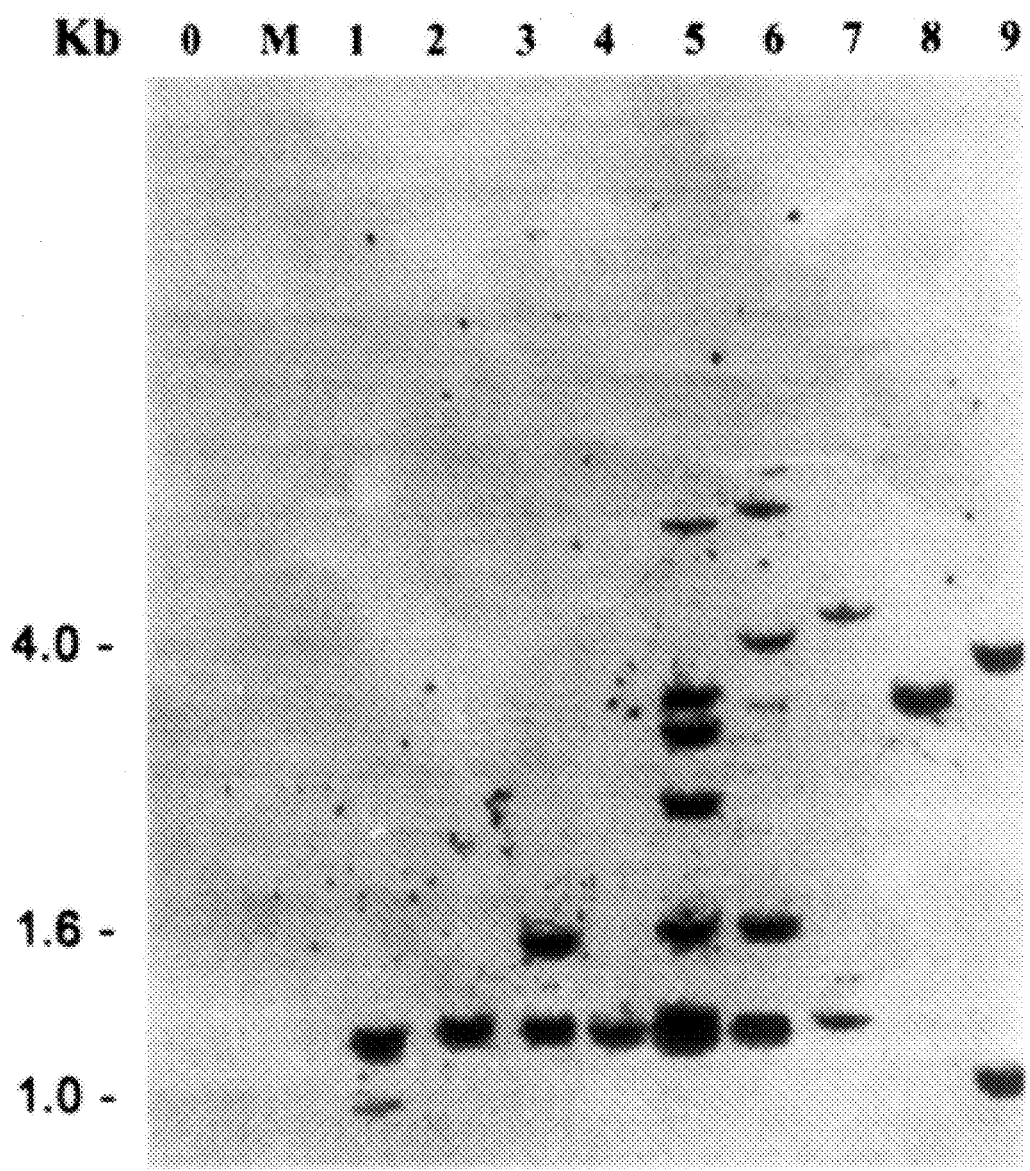

FIG. 4: Southern blot of the product of digestion of genomic DNA extracted from transgenic clones T0 of *Nicotiana tabacum* for antisense gene SGP-CP(-) 1–7) and from transgenic clones T0 of *Nicotiana tabacum* for sense SGP-CP(+) gene (8 and 9). The letter M indicates the well to which the product of digestion of the genomic DNA extracted from a non-transformed *Nicotiana tabacum* cv. W38 plant, used as control, was added.

Figure 5B:
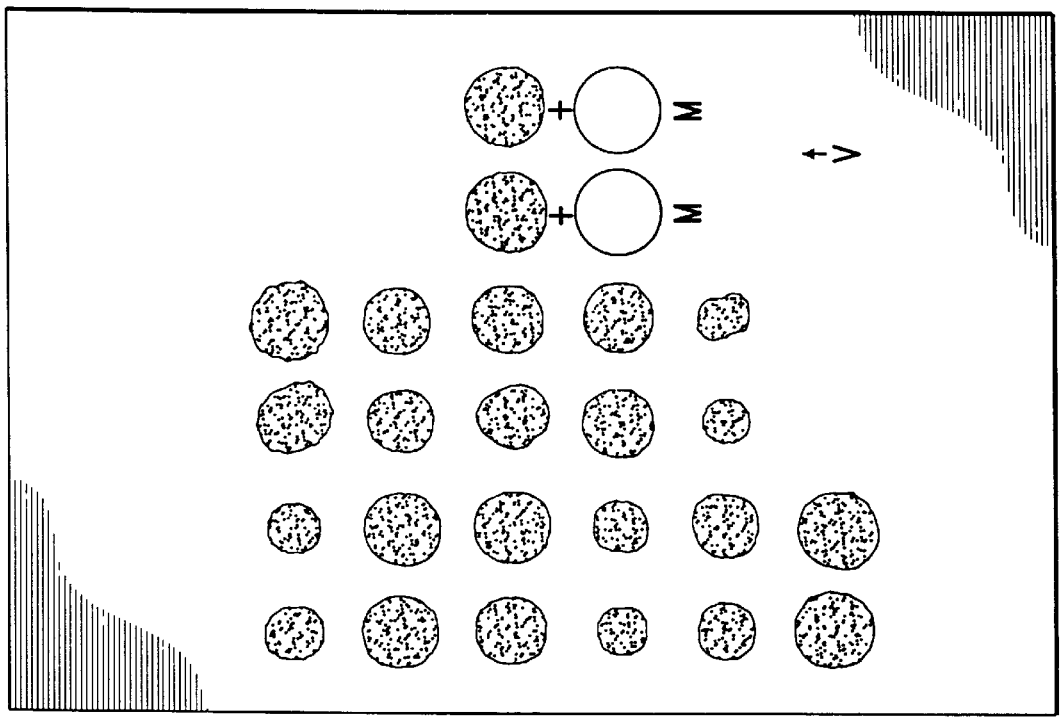
Figure 5A:
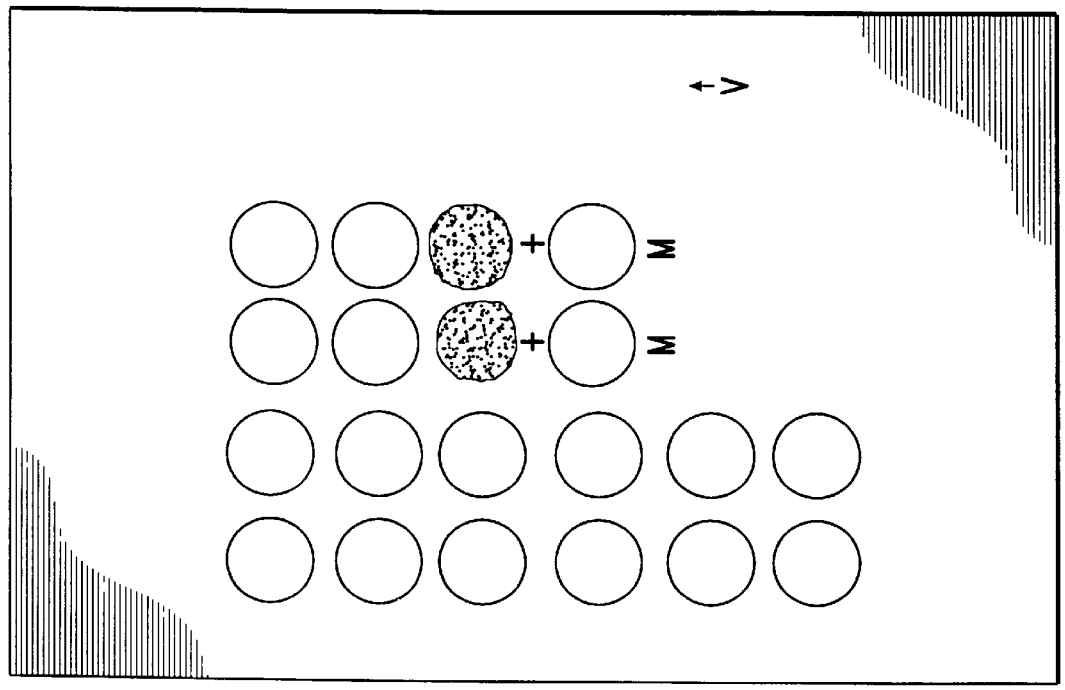

FIG. 5: Dot blot on transgenic plants infected with CMV. In A twenty samples are reported of transgenic plants T1, sixteen of which (marked with the circle) did not display any symptoms. In B twenty-six samples are reported of transgenic plants T1, twenty-two of which display the infection symptoms. The symbol "+" indicates two non-transgenic clones (positive control) infected by the virus; the letter M indicates the negative control, constituted by two non-transformed, non-infected plants; the letter V indicates the positive control given by the total nucleic acids of CMV virions extracted from infected tomato plants cv. Rutgers.

Figure 6:
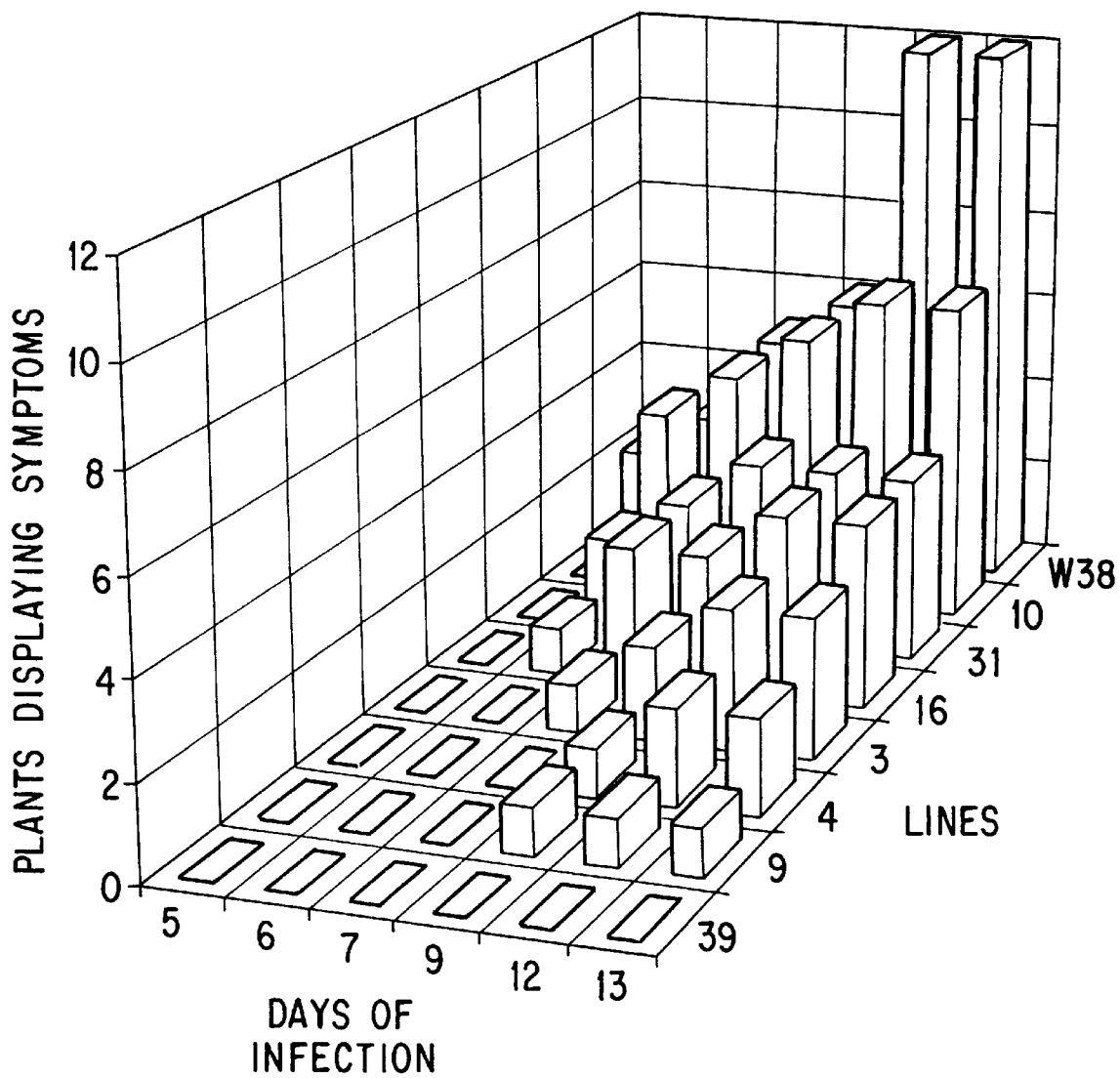

FIG. 6: The results are reported from the bioassay of the seven transgenic tobacco lines. On the abscissa, the time in days is reported; on the ordinate, the number is reported of plants which displayed the infection symptoms.

DETAILED DESCRIPTION OF THE INVENTION

The gene construct of the present invention can be prepared by conventional techniques, such as, e.g., Polymerase Chain Reaction (PCR), from a cDNA clone of viral RNA.

For exemplifying, non-limitative purposes, in the following disclosure the preparation is reported of a gene construct (also indicated as "SGP-CP gene") containing a portion of CMV RNA-3, with a part of the sub-genomic promoter.

In particular, said construct was prepared by amplifying a fragment of CMV cDNA-3 constituted by the domain F of the sub-genomic promoter, CP gene, its leader sequence and the 3'-terminal region (tRNA-like domain) of RNA-3.

The gene construct of the present invention is then introduced into a vector containing a promoter active in the plant cells in antisense orientation relatively to said promoter. For such a purpose, conventional methods can be used, which are based on the use of restriction enzymes.

Said vectors contain a promoter and a terminator which are functional in plant cells, and a suitable marker for in vitro selection of transformants, as, e.g., resistance to antibiotics.

Promoters which are active in plant cells include the promoters of nopaline synthase (NOS), octopine synthase (OCS) (present in tumor inducing plasmids of *Agrobacterium tumefaciens*), the promoters 19S, 35S and 35D of cauliflower mosaic virus (CaMV).

Examples of terminators are those of nopaline synthase (NOS), octopine synthase (OCS).

Examples of suitable vectors for the purposes of the present invention are, e.g., those which are derived from Ti plasmid of Agrobacterium tumefaciens, as reported by Bevan M., (1984), Nucleic Acid Research 12:8711–8721, such as pBin19, pBI121.1, pJAZZ, and so forth.

According to a preferred embodiment of the present invention, pJAZZ vector is used which comprises a CaMV 35S promoter, the terminator OCS and a chimeric gene NOS-NptII-NOS encoding resistance to kanamycin antibiotic.

The recombinant vector comprising the antisense gene construct of the present invention is then used in order to transform the plants using conventional methods. Preferably, the method is used which is described by G. An et al. (Binary vectors, Plant Molecular Biology Manual A3, Kluwer Academic, Dordrecht, pages 1–19, 1988), based on the capability by Agrobacterium tumefaciens of transferring a portion of its own DNA to plant cells.

The so transformed plants are then regenerated and tested for virus resistance, by exposing them to the virus at a concentration comprised within the range of from 1 to 20 µg/ml using conventional methods.

For example, for virus inoculation, a method can be used which involves abrading the leaves with an aqueous suspension, generally a buffer at pH 7–8, containing an abrasive material such as carborundum or celite, and the virus.

The regeneration system uses plant explants obtained from various organs of the plant, which are cultivated on a suitable substrate for callus formation and growth. The callus is then transferred to a regeneration substrate complemented with cytokinins in order to give rise to sprouts through the processes of adventitious embryonal differentiation, or organogenesis.

In the case of tobacco, callus formation and growth can be carried out by cultivating the transformants on a media selected, e.g., from MS, B5, Kao (8b), REG.

The resulting shoots are transferred on hormone-free regeneration medium and cultured until rooting and seedling formation.

The method according to the present invention enables the preparation of transgenic plants which display a complete resistance to CMV. The resistance manifests itself in a complete absence of symptoms and an evident incapability of virus spreading from the site of inoculation to the other parts of the plant.

The following examples are supplied for the purpose of better illustrating the present invention, without limiting it.

EXAMPLE 1

Construction of a Clone Comprising the cDNA of CMV-1 RNA-3

The viral genomic RNA was isolated from purified CMV-1 virions by extraction in phenol/SDS and then precipitating the nucleic acids by means of alcohol, according to Lot et al. (Ann. Phytopath., 4:25–38, 1972).

Genomic RNAs were then used in order to synthesize the total, single-stranded cDNA using an oligonucleotide (RNAREV) 5'TGG TCT CCT TTT GGA GGC CC (SEQ ID NO:4) 3' specific to the 3' terminal of all genomic RNAs of CMV-1.

In practice, 3 µg of genomic RNAs and 40 picomoles of RNAREV oligonucleotide were introduced into an Eppendorf tube and were allowed to stand at 65° C. for 3 minutes. After cooling the mixture in an ice bath, there were added 0.5 mM of each DNPT (dGTP, DATP, dTTP and dCTP), 1000 units of M-MVL reverse transcriptase (BRL), 10 µl of M-MLV buffer 5×, in an end volume of 50 µl. The resulting mixture was incubated at 37° C. for 1 hour. The total single-stranded cDNA was then purified by extraction with phenol:chloroform and was precipitated in ethanol by adding tRNA as carrier.

The so obtained cDNA was then used as template for the specific amplification of double-stranded cDNA of RNA-3 by using the RNA3FOR oligonucleotide 5'GTA ATC TTA CCA CTT GTG TG-3' specific to the 5'-terminal of this viral RNA in an amplification by PCR (Polymerase Chain Reaction) obtained as follows:

To 50 µl of reaction the following were added: 10 mM Tris-HCl pH 8.3, 50 mM KCl, 1.5 mM $MgCl_2$, 0.01% gelatin, 40 pmoles of each RNA3-FOR and RNA3-REV primer, 0.2 mM DNPT. The reaction was carried out with DNA Thermal Cycler® (Perkin-Elmer Cetus), as follows:

30 cycles of 2 minutes at 94° C., 2 minutes at 40° C., 2 minutes at 55° C., 3 minutes at 72° C. The 2.0 Kb long fragment corresponding to cDNA-3 was separated on 0.8% agarose gel, and was isolated by using the Gene Clean kit (BI0101 Inc., La Jolla, Calif., USA). 100 ng of this fragment was then ligated with 100 ng of pCR1000 vector of TA Cloning Kit (InVitrogen Inc.). 2 µl of ligase mixture was then used to transform E. coli DH5α cells made competent as described by Sambrook, J., Fritsch, E. F. and Maniatis, T. (1989), "Molecular Cloning: A Laboratory Manual", Cold Spring Harbor, N.Y., 2nd. Ed.. A clone containing the cDNA of RNA-3 of CMV-1 was identified by the restriction map of the plasmid DNA extracted by means of alkaline lysis, as described by Sambrook et al. This clone was denominated pCR-CMV1RNA3.

EXAMPLE 2

A fragment of 1066 bp constituted by the domain F of the sub-genomic promoter, CP gene, its leader sequence and 3'-terminal region (3'UTR) of RNA-3 was sub-cloned by starting from pCR-CMV1RNA3 clone, as obtained as reported in above example 1.

For that purpose, the PCR technique was used, by using, as primers, the following pair of oligonucleotides:

```
- 5'CCG GAT CCC ACT TTC TCA TGG 3' (SEQ ID NO:2) FORWARD and
     BamHI

- 5'CCG GAT CCT GGT CTC CTT TTG GAG GCC CCA 3' (SEQ ID NO:3)
     REVERSE BamHI
``` designed in the middle region of 5'-initial and 3'-terminal sub-genomic promoter and containing a BamHI restriction site useful for the subsequent cloning into the plant expression vector pJAZZ.

The oligonucleotides were synthetized by known methods, using the Gene Assembler Plus® (Pharmacia) synthetizer.

The amplification was carried out using a DNA Thermal Cycler® (Perkin-Elmer Cetus) apparatus, using a reaction mixture (50 μl) containing:

20 ng of cDNA-3 as template;

2.0 units of Taq polymerase (Boehringer);

10 mM Tris-HCl pH 8.3;

1.5 MM $MgCl_2$;

50 mM KCl;

0.01% gelatin (by weight/volume)

40 picomoles of each primer;

200 μM of each DNTP (dGTP, DATP, dTTP and dCTP).

After adding a paraffin bead (Ampliwax™ PCR Gem 100®-Perkin-Elmer Cetus), the cyclic program was started, which comprises:

1 minute at 94° C.;

1 minute at 55° C.;

1 minute at 72° C. for thirty cycles;

15 minutes at 72° C. (end extension).

The resulting amplification product was purified on 1% agarose gel using Gene Clean® kit (Bio 101, Inc. La Jolla Calif., USA) according to the protocol suggested by the manufacturer.

By operating as reported above, a band of 1.1 Kb bp was obtained, which corresponds to the fragment of interest.

100 ng of this fragment was ligated to pCR1000 plasmid (50 ng) and the ligation mixture was used to transform competent cells of *E. coli* DH5α (BRL). The transformants were screened on LB media [8 g/l Bacto Tryptone (DIFCO), 5 g/l NaCl, 15 g/l Agar (DIFCO), 0.5 g/l yeast extract] containing 50 μg/ml of kanamycin.

The plasmid DNA isolated from a positive clone was then analyzed by restriction map and sequence analysis by using the ABI dideoxyterminator® kit (ABI Perkin-Elmer Cetus) in order to verify that to the amplified sequence no mutations had been added during the amplification cycles. This plasmid was denominated pCR1000/SGP-CP.

EXAMPLE 3

Construction of the Recombinant Vector for Plant Transformation

Approximately 100 ng of pJAZZ1 vector (Clontech) was digested with BamHI restriction enzyme and the digestion fragments were ligated to SGP-CP fragment (100 ng) isolated from pCR1000/SGP-CP by digestion with BamHI.

An aliquot (2 μl) of ligation mixture was used to transform competent cells of *E. coli* DH5α. The transformants were subsequently screened on plates of LB media containing 50 μg/ml of kanamycin.

From the positive clones the recombinant plasmids were isolated which comprised SGP-CP gene in antisense (−) and sense (+) relatively to the promoter.

These plasmids were denominated pJAZZ-SGP-CP (−) (FIG. 2-B) and, respectively, pJAZZ-SGP-CP (+).

EXAMPLE 4

Transformation of *Agrobacterium tumefaciens*

Cells of *Agrobacterium tumefaciens* LBA4404 (Hockman et al., Nature 303:179–183, 1983) were transformed with the vectors pJAZZ-SGP-CP (−) and pJAZZ-SGP-CP (+), by triparental mating (Ditta et al., 1980, PNAS, 77 (12):7347–7351), with the *A. tumefaciens* [pJAZZ-SGP-CP (−)] and *A. tumefaciens* [pJAZZ-SGP-CP (+)] strains being obtained. The confirmation of occurred transfer was carried out by restriction analysis, PCR and hybridization with a $^{32}P$ labeled DNA probe having its sequence corresponding to SGP-CP fragment.

EXAMPLE 5

Transformation of *Nicotiana tabacum* Plants

Leaves of seedlings of *Nicotiana tabacum* L. (Wisconsin 38) cultivated in vitro at 25° C. to the stage of ⅔ leaves (16 hours light/8 hours darkness) under aseptic conditions, were used in order to prepare leaf disks of approximately 1 cm of diameter.

These disks were transformed by co-cultivation with a bacterial suspension of *A. tumefaciens* LBA4404 [pJAZZ-SGP-CP (−)] and *A. tumefaciens* [pJAZZ-SGP-CP (+)] having 0.6 O.D. (optical density) at 600 nm, in liquid MS media (Murashige and Skoog, 1962 Physiol. Plant. 15:473–497) at room temperature for 10 minutes. The leaf disks were then washed two-three times with sterile water in order to eliminate the bacterial excess (Horsch, R. B. et al., Science, 227:1229–1231, 1985) and were then regenerated on REG media (Horsch et al., 1985) containing 200 μg of kanamycin (Km). Approximately 2 weeks later, these disks produced calluses and after approximately 3–4 weeks, kanamycin-resistant calluses ($Km^R$) developed many shoots. $Km^R$ shoots were transferred to hormone-free MS media (Horsch et al., 1985) and many of them continued to grow in the presence of 200 μg of kanamycin/ml. The number of transformants obtained by means of the above reported method was of approximately 100.

EXAMPLE 6

Screening of Transformed Plants

Seven $Km^R$ plants (142-3, 142-4, 142-9, 142-10, 142-16, 142-31 and 142-39) coming from independent regenerations (T0) were submitted to screening by PCR amplification and Southern blot in order to verify whether the integration had occurred of T-DNA into the plant genoma.

A) Polymerase Chain reaction

Genomic DNA extracted from each plant as described by Della Porta et al. (Plant Mol. Biol. Rep., Vol. I, 4:19–21, 1983) was submitted to amplification by PCR, using as primers the oligonucleotides having the sequences as reported in Example 2.

The amplification was carried out on a DNA Thermal Cycler® apparatus (Perkin-Elmer Cetus), by using a reaction mixture (50 μl) containing:

400 ng of genomic DNA;

40 picomoles (pmoles) of each primer;

200 μM of each DNTP (dATP, dGTP, dTTP, dCTP);

2.5 U of Taq DNA Polymerase (Boehringer Mannheim) with 5 μl of 10×Taq buffer (Boehringer Mannheim).

The cyclic program comprised:

5 minutes at 95° C.;

15 seconds at 95° C.; 1 minute at 60° C.; 3 minutes at 72° C. during 35 total cycles; and 10 minutes at 72° C.

Ten μl of the reaction mixture was analyzed by electrophoresis on 1% agarose gel and subsequent staining with ethidium bromide (2 μg/ml). The results displayed in FIG. 3 show, as expected, the presence of a band at approximately 1.1 Kb. On the contrary, such band was absent in the negative controls, constituted by the product of reaction on genomic DNA extracted from a non-transformed W38 tobacco plant and the genomic DNA-free reaction mixture.

B) Southern blot

Ten μg of genomic DNA was digested with restriction enzyme HindIII (Boehringer Mannheim), a 1% agarose gel was loaded with the digestion mixture and submitted to electrophoresis. DNA was transferred to Hybond-N(+)® membrane (Hamersham) and was hybridized to the $^{32}$P labeled DNA probe reconstructed from cDNA clone of RNA-3 [Sambrook and Fritsch, E. F. and Maniatis, T. (1989), Molecular Cloning: A Laboratory Manual, (Cold Spring Harbor Lab., Cold Spring Harbor, N.Y.) 2nd Ed., 1989].

The screened plants showed the presence of chimeric tDNA, in a variable number of copies from 1 (FIG. 4, wells 3 and 7) to at least 5 (FIG. 4, wells 5 and 6).

T0 plants were transferred to pots containing soil and the pots were placed into containment controlled-atmosphere chambers, inside which they were grown until they flowered and self-pollinated. Then, the ripen seeds of T1 generation were collected and used for the subsequent screening operations.

T1 seeds were sterilized and were caused to germinate in vitro on MSO media (Murashige T. and Skoog F., Physiol. Plant, 15:473–497, 1962) containing 200 mg of kanamycin/l. By operating in that way, only those seeds were selected which contained the chimeric gene NptII associated with SGP-CP(-) gene.

After germination, the individual T1 seedlings were further checked by PCR analysis with oligonucleotides having such sequence as reported in Example 2. As expected, the obtained results showed that all T1 plants displayed the presence of the band at about 1.1 Kb, corresponding to SGP-CP(-) gene.

EXAMPLE 7

Infection of Transgenic Plants (Bioassay)

Twelve randomly selected T1 seedlings, for each of seven T0 clones, were transferred to small pots containing soil. After three weeks of transfer, they were inoculated with purified virions from tomato plants cv. Rutgers (Lot et al., Ann. Phytopathology 4:25–38; 1972). On two apical leaves a small abrasion was first produced with celite and, later on, on each leaf 10 μl was distributed of a concentrated solution (20 μg/ml) of satellite-free CMV virions in 20 mM phosphate buffer pH 7.2. After slight rubbing with a sterile swap to distribute the virions, the leaves were washed with sterile distilled water in order to remove celite excess. As control, non-transformed plants of N. tabacum cv. W38 were used.

The results reported in FIG. 6 demonstrate that the line 142-39 displays absolute resistance (resistance level 100%), whereas the line 142-10 displays a 50% resistance. Furthermore, one may observe that, starting from the fifth day of infection, two from the twelve control plants displayed infection symptoms, reaching the 100% infection level on the twelfth day. Furthermore, all plants of transgenic lines which endowed with sensibility showed an evident slacking down of the infection, with the observed symptoms being much milder than of control.

EXAMPLE 8

In order to verify the hypothesis that the resistance shown by T1 plants was not associated to a probable production of capsidic protein, an ELISA assay was carried out using specific antibodies raised against Coat Protein (CP).

Resistant plants of T1 line 142-39 were used, and were compared to plants of T1 lines derived from two transgenic clones for SGP-CP gene in sense orientation.

The presence of the coat protein was detected by the classic sandwich double antibody ELISA technique.

The ELISA assay was carried out by using Nunc 96-flat-bottom-wells plates for microtitrations (Nunc-Immunoplate 1, Nunc, Roskilde, Denmark). The plates were incubated overnight at room temperature (20–25° C.) in a wet chamber with 200 μl/well of a solution containing anti-CMV IgG antibody diluted 1:200 with coating buffer (1.59 g/l Na$_2$CO$_3$, 2.93 g/l NaHCO$_3$ and 0.20 g/l NaN$_3$ pH 9.6). After incubation at 37° C. for 4 hours, the solution was removed from the wells and the plate was washed 4 times with the washing buffer (8.0 g/l NaCl, 2.9 g/l Na$_2$HPO$_4$×12 H$_2$O, 0.2 g/l K$_2$HPO$_4$, 0.2 g/l KCl, 0.2 g/l NaN$_3$ and 0.5 ml/l Tween 20, pH 7.2–7.4).

Total protein was extracted from 300 mg of green tissue collected from tobacco plants grown in vitro to the second/third leaf stage, by operating according to Sanofi protocol (Phyto-Diagnostics). 200 μl of clarified extract was then added in duplicate to each well of the microplate and the wells were incubated overnight at 5° C. After removing the reaction solution and five washes with washing buffer, to each well 200 μl was added of anti CMV-AP IgG antibody-alkaline phosphatase conjugate diluted 1:200 in the extraction buffer. The reaction was carried out at 37° C. for 4 hours. After removing the solution excess and five washes with washing buffer, to each well 200 μl was added of specific substrate pNPP (1 mg/ml) in diethanolamine buffer (97 ml/l diethanolamine, 0.2 g/l MgCl$_2$×6 H$_2$O, 0.2 g/l NaN pH 9.8). The plates were incubated at room temperature for 1.5 hours.

The optical density reading was carried out at 405 nm with a Lambda Reader spectrophotometer (Perkin-Elmer). The results, expressed as average OD and standard deviations obtained from two replicates of four plants are reported in Table 1.

TABLE 1

| Tobacco samples | Lines | OD405 nm |
|---|---|---|
| Transformed with SGP-CP (−) gene | 142–39 | 0.060 ± 0.013 |
| Transformed with SGP-CP (+) gene | 131–43 | 0.390 ± 0.072 |
| Transformed with SGP-CP (+) gene | 131–30 | 0.280 ± 0.040 |
| Non-transformed W38 | — | 0.103 ± 0.015 |
| W38 infected with CMV | — | 0.884 ± 0.040 |

From the data reported in Table 1 one will see, as expected for an antisense construct, that CP is not produced in the tissues of the transgenic plants containing SGP-CP(−) gene.

Consequently, resistance displayed by antisense clones is apparently mediated by RNA, and, on the contrary, is not correlated to the protection mediated by the coat protein.

EXAMPLE 9

Molecular Analysis by Dot Blot

Total nucleic acids were extracted from 200 mg of plant tissue using an extraction buffer having the composition 50 mM NaOH, 2.5 mM EDTA pH 8 with a ratio of 1:1 by weight/volume.

Five μl of clarified extract were spot distributed on Hybond-N filter with the respective dilutions being carried out with the same extraction buffer. As the probe, the gene was used which encodes 3a protein obtained by synthesis of cDNA on 5' portion of CMV RNA-3. The hybridization was carried out by using 1 ml/cm$^2$ of a solution of 50% formamide, 5×SSC, 2% Blocking Reagent (Boehringer), 0.1% Sarcosyl® and 0.02% SDS and the probe at 1×10$^6$ CPM/ml. After four washes, two washes at room temperature for 5 minutes with 2×SSC 0.1% SDS and two washes at 68° C. for 15 minutes with 0.1×SSC 0.1% SDS, the filters were used to expose Kodak X-Omat plates at −80° C. The results reported in FIG. 5 demonstrate that in resistant plants this character does not only suppress the appearance of the symptom, but is associated with a complete absence of CMV in non-inoculated leaves, as demonstrated by (FIG. 5, A). On the contrary, susceptible T1 transgenic plants, similarly to non-transformed W38 tobacco plants, showed the presence of a high level of CMV in their tissues, indicating that virus had spread from the inoculation site to the residual parts of the plant (FIG. 5, B).

EXAMPLE 10

Resistant plants of T1 offspring were cultivated, grown until they flowered, and self-pollinated in order to produce T2 seeds, evidencing a normal and completely healthy phenotype. Non-transgenic tobacco plants showed serious symptoms: reduced vegetative growth (dwarfism), diffused chlorosis throughout the plant (mosaic), associated with a high viral titre (FIG. 5, +). Inoculated leaves of some resistant plants showed chlorotic injuries at the inoculation site, with infection not systemically diffusing to the residual aerial parts of the plants. These observations would indicate that the resistance is strongly correlated to an inhibition of long-distance movement (Gilbertson et al., 1993), or to a localization of replication at infection sites.

---

What is claimed is:

1. A method of preparing transgenic plants resistant to infections caused by RNA-viruses, comprising integrating into the genome of said plants an antisense gene construct comprising:
   (a) an F domain of a subgenomic promoter of cucumber mosaic virus (CMV);
   (b) downstream from said sub-genomic promoter, a leader sequence of a coat protein gene of CMV;
   (c) downstream from said leader sequence, a gene encoding a CMV coat protein; and
   (d) downstream from said gene, a 3'-terminal region of a CMV coat protein gene.

2. The method according to claim 1, wherein the antisense gene construct comprises SEQ ID NO:1.

3. A recombinant vector comprising:
   (a) a promoter which functions in a plant;
   (b) downstream from said promoter,
      (i) an antisense gene construct comprising an F domain of a sub-genomic promoter of CMV;
      (ii) downstream from said sub-genomic promoter, a leader sequence of a coat protein gene of CMV;
      (iii) downstream from said leader sequence, a gene encoding a CMV coat protein; and
      (iv) downstream from said gene, a 3'-terminal region of a CMV coat protein gene; and
   (c) a terminator which functions in the plant.

4. The recombinant vector of claim 3, wherein said promoter is selected from the group consisting of a nopaline synthase (NOS) promoter, an octopine synthase (OCS) promoter and promoters 19S, 35S and 35D of cauliflower mosaic virus (CaMV).

5. The recombinant vector of claim 3, wherein said terminator is selected from the group consisting of a terminator of nopaline synthase (NOS) or a terminator of octopine synthase (OCS).

6. The recombinant vector of claim 3, wherein said antisense gene construct comprises SEQ ID NO:1.

7. A transgenic plant resistant to viral infections obtained by the method of claim 1.

* * * * *

CERTIFICATE OF CORRECTION

PATENT NO. : 5,959,181

DATED : September 28, 1999

INVENTOR(S): Francesco CELLINI et al.

It is certified that an error appears in the above-identified patent and that said Letters Patent is hereby corrected as shown below:

On the title page, item [30], the Foreign Application Priority Data has been omitted. It should be:

--[30]  Foreign Application Priority Data

May 9, 1996  [IT]  Italy.................MI96/A/000927--

Signed and Sealed this

Twentieth Day of June, 2000

Attest:

Q. TODD DICKINSON

Attesting Officer

Director of Patents and Trademarks